United States Patent [19]
Williams

[11] Patent Number: 4,936,760
[45] Date of Patent: Jun. 26, 1990

[54] VOLUMETRIC INFUSION PUMP

[76] Inventor: David R. Williams, 11323 Capilla Rd., San Diego, Calif. 92127

[21] Appl. No.: 364,836

[22] Filed: Jun. 12, 1989

[51] Int. Cl.⁵ ............................................. F04B 43/08
[52] U.S. Cl. .................................... 417/479; 417/478; 604/153
[58] Field of Search ............... 417/474, 476, 477, 478, 417/479, 480; 604/153, 151, 250; 128/DIG. 12

[56] References Cited

U.S. PATENT DOCUMENTS

| | | | |
|---|---|---|---|
| 2,351,828 | 6/1944 | Marsh | 604/153 X |
| 2,917,002 | 12/1959 | Mascaro | 417/477 |
| 3,518,033 | 6/1970 | Anderson | 417/478 |
| 3,565,554 | 2/1971 | Muller | 417/477 |
| 3,606,596 | 9/1971 | Edwards | 417/479 |
| 4,178,138 | 12/1979 | Iles | 417/477 X |
| 4,273,121 | 6/1981 | Jassawalla | 417/478 X |
| 4,479,797 | 10/1984 | Kobayashi et al. | 417/474 X |
| 4,565,542 | 1/1986 | Berg | 604/153 X |
| 4,781,548 | 11/1988 | Alderson et al. | 417/478 X |
| 4,872,813 | 10/1989 | Gorton et al. | 417/479 X |

FOREIGN PATENT DOCUMENTS

| | | | |
|---|---|---|---|
| 0255538 | 1/1949 | Switzerland | 417/476 |
| 0620870 | 3/1949 | United Kingdom | 417/474 |

Primary Examiner—Leonard E. Smith
Assistant Examiner—Eugene L. Szczecina
Attorney, Agent, or Firm—John J. Murphey

[57] ABSTRACT

A non-peristaltic infusion pump having improved accuracy and reliability including a novel infusion pump module having an elongated flexible lumen chamber defined by broad, slightly rounded upper and lower chamber walls joined along sharp side corners and having exterior graspable handles and a machine for holding the module by the handles between reciprocating jaw assemblies that slightly distend and slightly compress the module walls in coaction with C-shaped valve members to develop the pumping action.

21 Claims, 5 Drawing Sheets

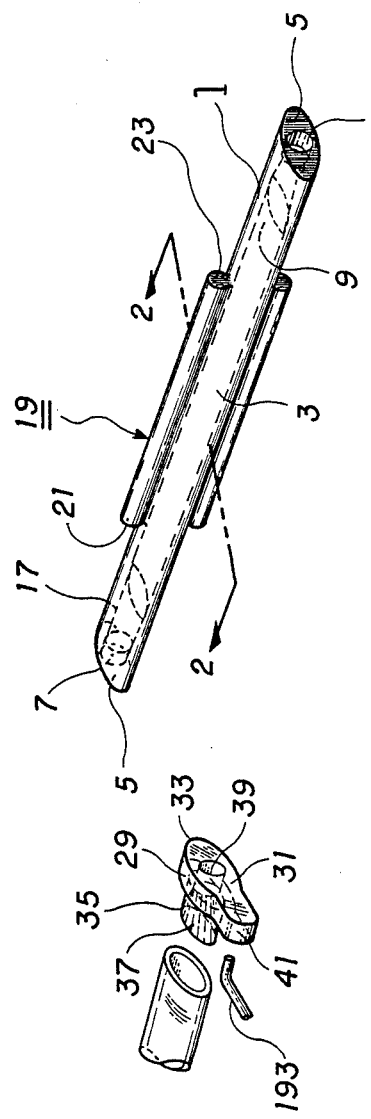
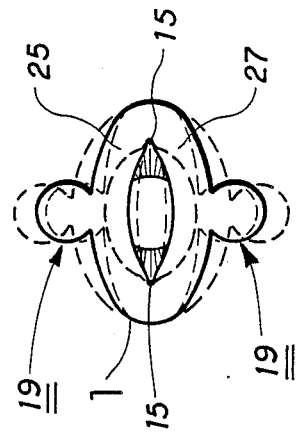
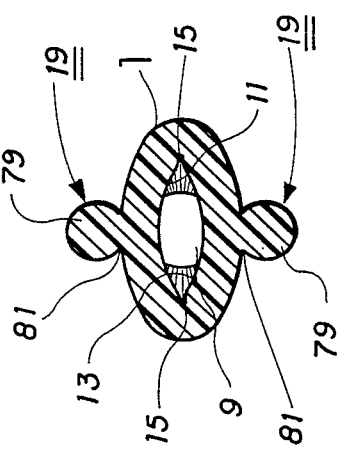
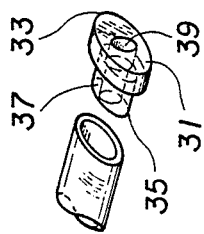
FIG. 1c
FIG. 1a
FIG. 3
FIG. 1b
FIG. 2

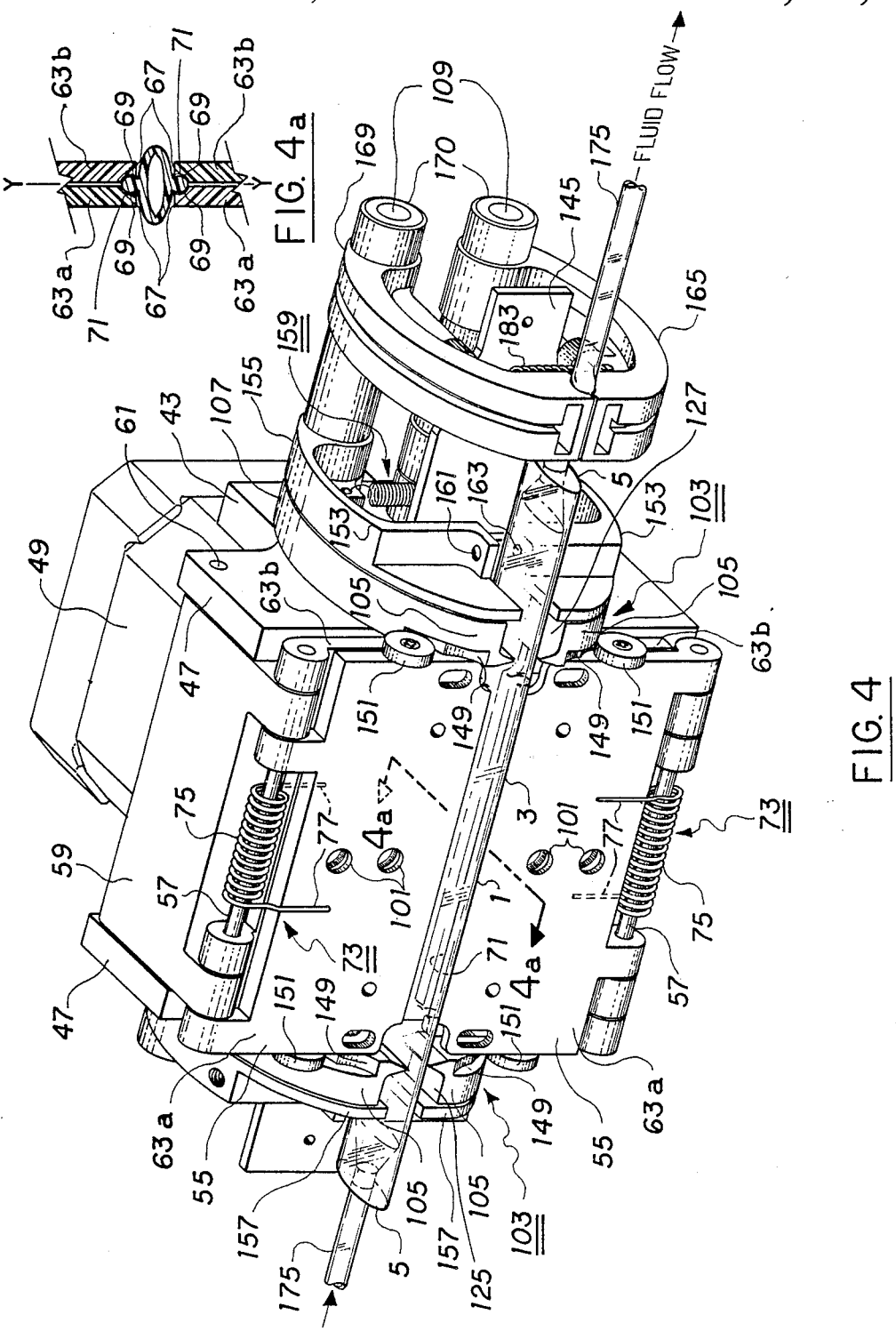

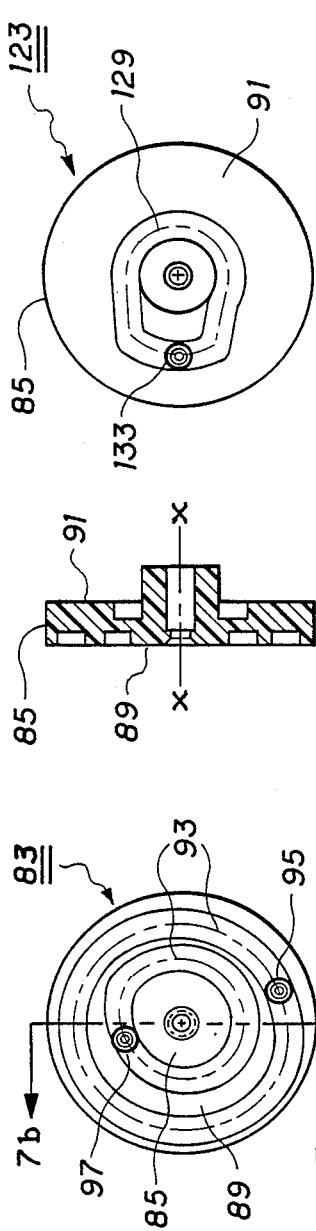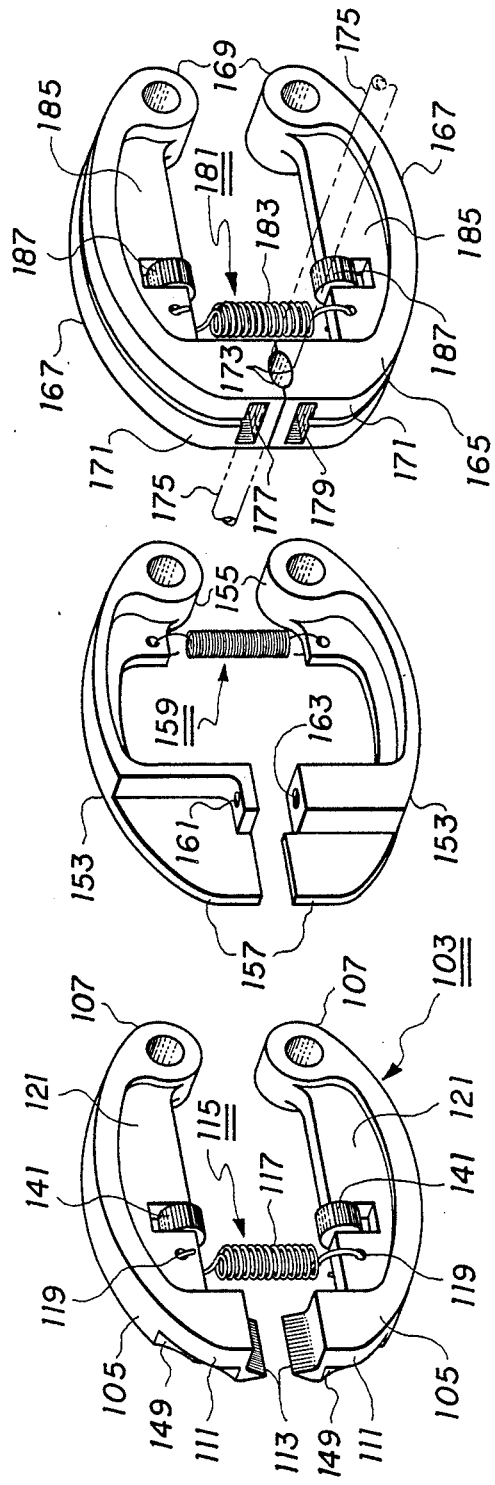

VOLUMETRIC INFUSION PUMP

BACKGROUND OF THE INVENTION

1. Field of the Invention

The present invention relates generally to fluid infusion systems and more particularly to an improved flow-metering apparatus for forcibly introducing a fluid into a positively pressured system such as the human body.

2. Description of the Prior Art

There are numerous types of pumps used to forcibly infuse liquids into the human body. Most of these pumps are of the peristaltic type wherein a round flexible tube (lumen-defining member) filled with the fluid is milked by continuous compression of the tube walls toward each other in a wavelike motion along a length of the tube to produce the pumping action. These peristaltic pumps rely on the memory of the elastomeric materials making up the tube walls to reset the internal volume, to determine pumping accuracies, and to provide reinflation power to the pump to draw more fluid from the reservoir to be pumped into the patient.

A number of problems have been created by the peristaltic nature of these pumps and further from the continuous compression-release cycle applied to the flexible tubing. The lumen-defining member is typically a cylindrical tube made of silicone rubber that demonstrates variable rebound characteristics with temperature and age. Peristaltic pumping causes significant stress to be placed on the elastomeric tube wall. Repeated compression-release cycling raises the stress at the area of the most abrupt change in curvature, namely the areas along the sides of the tube transiting the upper and lower wall segments. This repeated stress of pumping causes small bits of wall material to flake off and enter the stream of flowing fluid to either pass into the patient's body as a foreign substance or create an occlusion down stream to interrupt or diminish the flow of fluid thereby ruining the accuracy of the peristaltic pump.

Still further, the total collapse or pressing together of the lumen-defining member during the peristaltic pump action causes some compression of stream material between those wall sections. While homogeneous fluids are not greatly affected by this action, other types of fluids that include minute entrainments such as blood cells in a blood transfusion will cause cell damage and thereby deteriorate the quality of the infused material. Finally, these peristaltic pumps are very complex and include numerous parts that must be maintained freely mobile in the pump assembly to bring about the peristaltic action. Any leakage of fluid into these mechanisms thereby poses substantial sticking and malfunction of the pump components. The peristaltic pump components are susceptible to damage from spills of medicinal liquids either through cracking of the lumen-defining member or whenever the bag from which the contents are drawn breaks or cracks.

SUMMARY OF THE INVENTION

The present invention was developed in order to overcome the above and other problems encountered in conventional peristaltic infusion pumps and has as its main objects the provision of an infusion pump with improved short and long-term rate and volume accuracies as well as greatly reduced incidents of spallation of the lumen-defining member into the infused fluids. In addition, the pump is mechanically enclosed with only a slit in the front of the unit to reduce susceptibility to leakage and jamming of the pump apparatus. These objects are met in the inventive nonperistaltic infusion pump hereinafter described while, at the same time, providing improved output pressure sensing and input occlusion detection as well as a simplified mechanism of disengaging and unloading the pump mechanism for quick removal and replacement of the lumen-defining member. The pump apparatus is of small physical size and concomitantly low-power consumption. The nature of the lumen-defining member and the activity generated therewith by the volumetric pump of this invention greatly removes the volumetric inaccuracies that were occasioned with the prior art devices.

This unique combination of advantages is obtained by the discovery of an improved infusion pump module that comprises a length of resilient material having formed therein an elongated lumen chamber defined by slightly rounded, upper and lower lumen chamber walls joined together along sharp side corners, the module having opposed, outwardly-facing top and bottom exterior graspable handle means extending along a portion of the module and a pump that is designed to grasp the handle means and move the upper and lower chamber walls in reciprocal motion i.e., toward and away from each other, in conjunction with inlet and outlet valves to provide pumping action in combination with high-quality, long-term volumetric reproduceability. The upper and lower chamber walls of the pump module are passed through cyclic slight extensions and slight contractions on both sides of the neutral wall position but at no time are the chamber walls brought into contact with each other except at the valves. The walls are joined along sharp side corners throughout the length of the module which greatly reduces the energy required to close the flow area for valving. These sharp corners reduce, and in many cases, eliminate the stresses normally built up when a round tube is squashed together as in the prior art. Because of the mild partial distension and compression of the upper and lower lumen-defining chamber walls, with its concomitant elimination of stresses built up at the joint therebetween, the spallation problem has been virtually eliminated. In addition, with the upper and lower chamber walls being positively moved throughout their full range of motion, not depending upon elastomeric memory to re-inflate the tube, variation in volumetric accuracy is also virtually eliminated. Combining these features results in an infusion pump of greatly improved volumetric accuracies, both short and long term, without the stress problems and spallation problems associated with the prior art devices.

Accordingly, the main object of this invention is an infusion pump of superior volumetric accuracy. Other objects of the invention include an infusion pump with reduced spallation in the lumen-defining member, and greatly reduced costs in the manufacture of the lumen member by using materials such as thermoplastic elastomers which have poorer memory characteristics but are very low cost and offer greatly improved spallation performance.

These and other objects, affects and features and advantages will become more apparent from the following description of the preferred embodiments thereof taken in conjunction with the accompanying drawings.

DESCRIPTION OF THE DRAWINGS

FIG. 1a is an isometric view of one embodiment of the fusion pump module of this invention; FIG. 1b is an isometric view of one embodiment of an insert for positioning in the end of the fusion pump module shown in FIG. 1a; and, FIG. 1c is another isometric view of another embodiment of an insert for insertion in the end of the fusion pump module shown in FIG. 1a;

FIG. 2 is an elevational end view in cross-section of the module in its relaxed position and taken along lines 2—2 in FIG. 1;

FIG. 3 is the same elevational end view of FIG. 2 showing the limits, in dotted outline, of the slight extension and slight compression applied to the upper and lower chamber walls of the pump module during pump action;

FIG. 4 is a trimetric front elevational view of the preferred embodiment of the volumetric pump of this invention; FIG. 4a is an enlarged view of the jaw assemblies holding the pump module in its operative position;

FIGS. 7a, 7b and 7c are views of the cam wheel that drive the jaw assemblies of this invention, FIG. 7a showing the front cam grooves, FIG. 7b showing a side elevational cross-sectional view of the wheel taken along lines 7—7 in FIG. 7a, and FIG. 7c showing the rear view of the cam wheel and the cam groove formed therein;

FIG. 8 is an isometric view of one embodiment of the pinchoff valve mechanism of the invention;

FIG. 9 shows an isometric view of one embodiment of the means for determining the presence of occlusions in the fluid stream in said lumen chamber; and, FIG. 10 shows in isometric view one means for determining the presence of gas bubbles in the fluid stream in said lumen chamber.

DESCRIPTION OF THE PREFERRED EMBODIMENT

Figure 5:
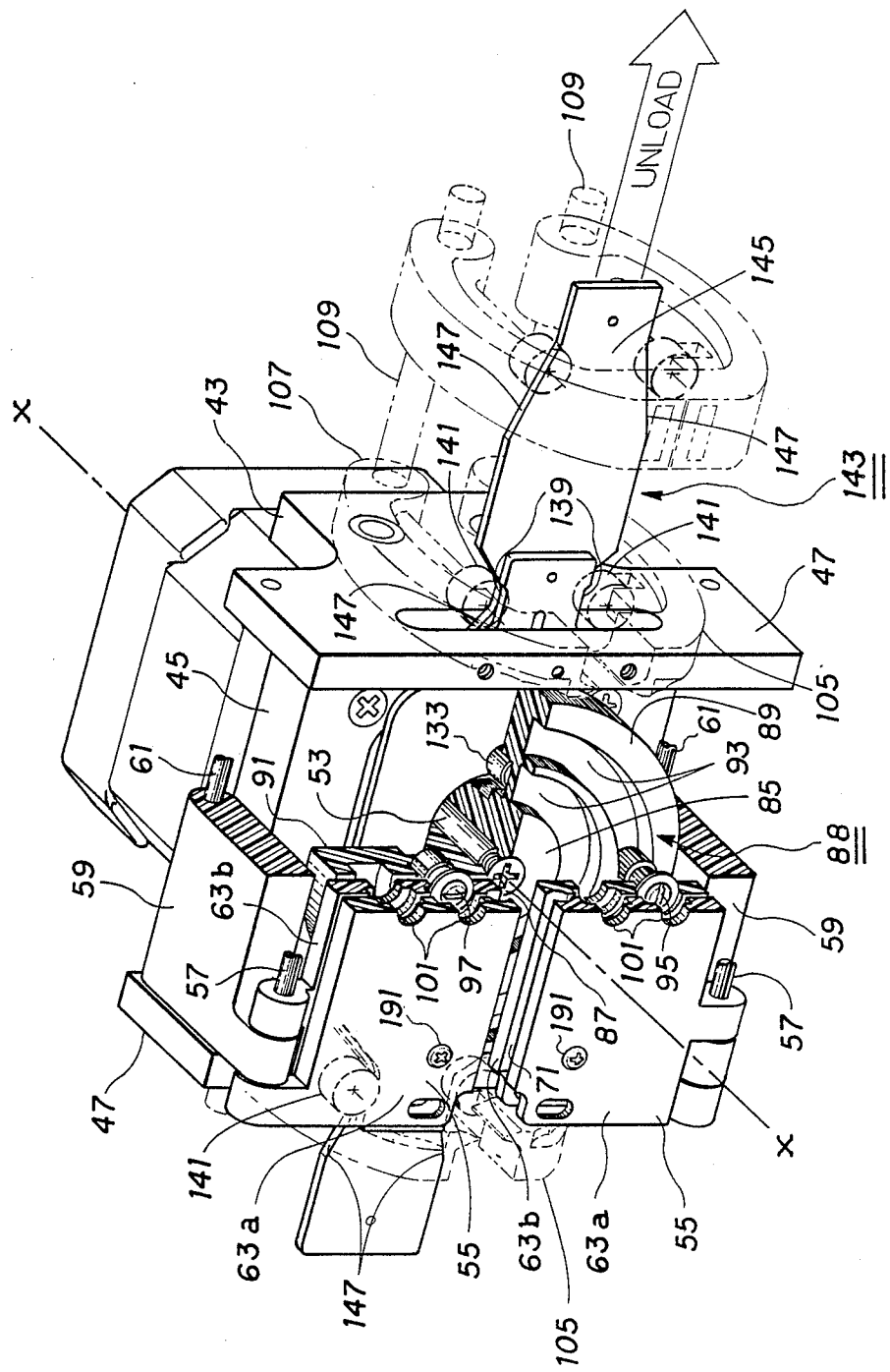
FIG. 5 is a trimetric front elevational view, partly in section, of the same embodiment shown in FIG. 4 with some of the valve mechanisms, pressure sensor mechanism and gas-bubble entrapment mechanism shown in phantom outline with the cam wheels associated therewith.

FIG. 1a shows one embodiment of the infusion pump module 1 of this invention and is shown to comprise a length of resilient material 3 that can be made of a wide variety of resilient materials, generally in polymeric form, such as natural rubber, synthetic rubber, blends of latex rubber and other polymeric materials including polyvinyl chloride, polyurethane, blended styrene compounds, etc. Module 1 is terminated by opposed, spaced-apart ends 5 in which are formed an aperture 7 preferably of a circular configuration. Interior of module 1 is formed an elongated lumen chamber 9 that transitions the greater part of the length of module 1 and is defined as shown in FIG. 2, by slightly rounded, upper and lower chamber wall surfaces 11 and 13 respectively, that are joined together along sharp inside side corners 15. Chamber 9 joins apertures 7 inboard of each end 5 through a transition segment shown in dotted outline at 17. Exterior, graspable handle means 19, terminated at spaced-apart ends 21 and 23, extend along a portion of module 1, preferably interior of said ends 5 and central therebetween, and extend outwardly, i.e., upwardly and downwardly, from top and bottom module walls 25 and 27 respectively.

Another embodiment of infusion pump module 1 is shown in FIG. 1b to comprise a module having the overall internal oval shape throughout its entire length from end 5 to end 5 and insert 29 used in each end to transition from the oval shape interior of module 1 to the circular shape needed for the transfer tube from the reservoir holding the liquid to be pumped into the patient's body at one end of module 1 and the circular tubing for attachment at the other end of module 1 to connect to the hypodermic needle used to insert the fluid into the patient's vein. Insert 29 is shown to comprise an end piece 31 having an outside edge 33 in the size and overall shape of the outside of pump module 1 to which is connected a short insert segment 35, having an outside wall 37 conforming to the size and shape of the inside cavity of pump module 1 and of a short length for insertion in said pump module cavity in end 5. A circular bore 39 is formed in end piece 31 extending inward through short insert segment 35 and gradually fanning out into a shape similar to that of the interior of pump module 1 to provide for a transition from the circular bore to the size and shape of the internal cavity in lumen chamber 9.

A similar insert 29 is shown in FIG. 1c wherein circular bore 39 is continued in its same size and shape through short insert segment 35 to empty directly into the internal cavity of pump module 1. Further, end piece 31 is shown in FIG. 1b to contain a tab 41 extending beyond the outer diameter of pump module 1 for contact with a switch or other arming device as will hereinafter be more fully explained.

Figure 6:
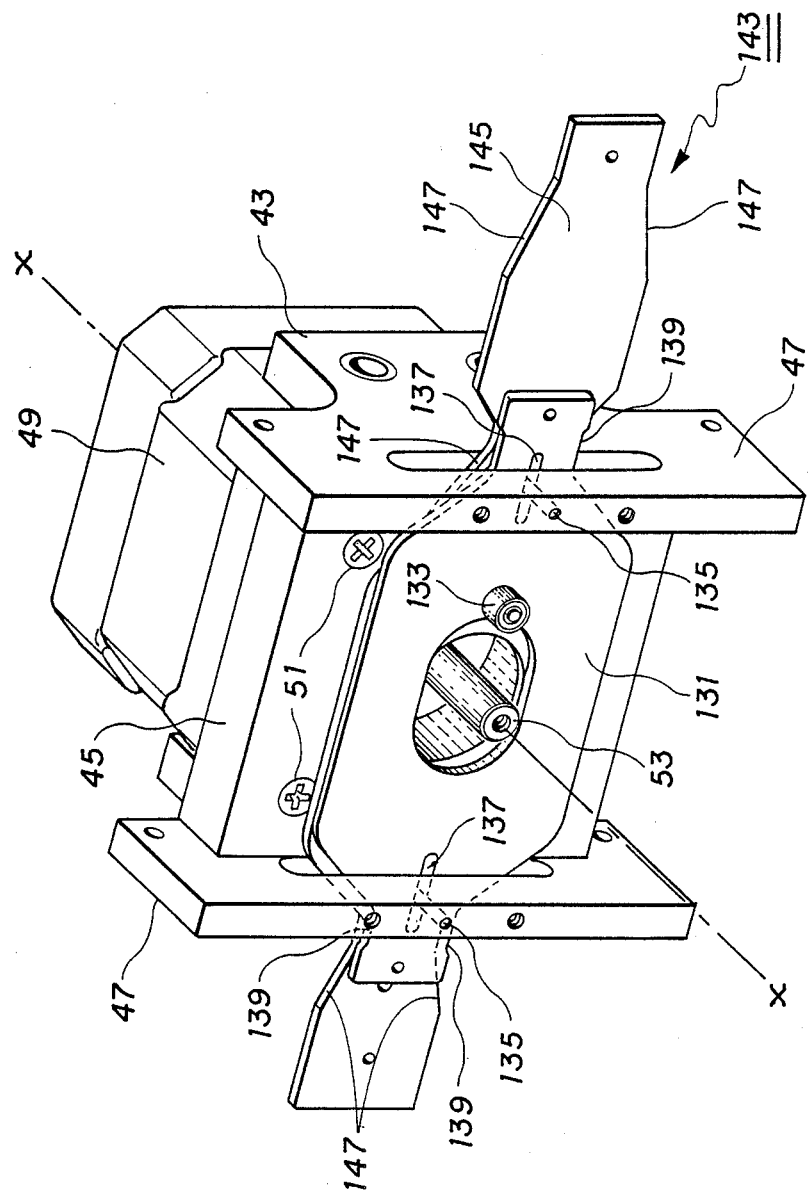
FIG. 6 is a trimetric front elevational view of the embodiment shown in FIGS. 4 and 5, with the jaw assemblies and cam wheel removed to expose slider cam plates and their relation to the chassis.

As can be seen in FIGS. 5 and 6, the volumetric fluid pump of this invention comprises a chassis 43 that is itself comprised of a backing plate 45 bounded between and integral with a pair of spaced-apart, mutually opposed end walls 47. A motor 49 is attached to chassis backing plate 45 with machine screws 51 and has a shaft 53 extending forward through an aperture in backing plate 45. Shaft 53 is driven by motor 49 in powered rotation about a fixed axis x—x as is shown in FIGS. 4, 5 and 6. While not critical to the operation of the inventive pump, it is preferred that motor 49 be a stepping-type motor or a geared D.C. motor.

As shown in FIG. 4, a pair of hinged jaw assemblies 55 are pivotally attached by a pair of spaced-apart first hinge pins 57 through a pair of top and bottom mounted pivot brackets 59 and through a pair of spaced-apart second hinge pins 61 to opposed end walls 47.

Jaw assemblies 55 are arranged vertically at the front of the apparatus and further are arranged in spaced-apart, opposed juxtaposition so that they face each other while in the vertical plane. Jaw assemblies 55 are preferably identical in size, shape and components and can be seen in FIGS. 4a and 5 to comprise a pair of flat, plate-like jaw members 63a and 63b adapted to fold together through mutually aligned pairs of offset ears pivotally mounted on first hinge pin 57.

Each jaw member 63a and 63b is defined by a lower edge 67, when folded together, that are adapted to coincide and lie in spaced-apart juxtaposition far enough apart to accept module 1 therebetween. As shown in FIG. 4a, each of jaw members 63a and 63b has formed, along their respective lower edges 67, a portion of a groove 69 that, when said jaw members are brought into aligned contact, form a full groove 71 along lower edges 67 as shown in FIG. 4a. When aligned in spaced-apart, opposed juxtaposition, grooves 67 are placed in mutual, spaced-apart opposition along the plane Y—Y formed by the mating surfaces of jaw members 63a and 63b.

Bias means 73, such as a coil spring 75 is shown in FIG. 4 to be wrapped about first hinge pins 57 in FIG. 4, having ends 77 that bear against jaw members 63a and 63b to urge them into adjacent mutual contact so that said groove portions 69 will close together and grasp handle means 19 of pump module 1 to hold said module between opposed lower edges 67 and retain it therein during operation of said pump.

As shown in FIGS. 2 and 3, handle means 19 is preferably made in a configuration including an elongated first portion 79 extending outward from top and bottom module walls 25 and 27 respectively, and separated therefrom by an elongated, narrow second portion 81. In addition, it is preferred that groove portions 69 are formed in a mirror image so that there is formed a tight connection between module top wall and bottom wall 25 and 27 and jaw members 63a and 63b when closed thereover.

A first cam and cam follower means 83 is shown in FIGS. 5 and 7a to be interconnected between shaft 53 and jaw assemblies 55 for driving the assemblies as a function of the motor-powered rotation of shaft 53 in mutually opposed reciprocal motion to slightly distend and slightly depress chamber upper and lower walls 25 and 27 equally along the length thereof to produce a pumping motion as is shown in dotted outline in FIG. 3.

First cam and cam follower means 83 is shown to comprise a wheel 85 attached to shaft 53 through a machine screw 87 so as to be normal to axis x—x. Wheel 85 contains first and second parallel mutually opposed wheel faces 89 and 91 respectively. First camming grooves 93 are formed in first wheel face 89; the full tracks of grooves 93 are shown in FIG. 7a. First and second cam follower assemblies 95 and 97 are respectively attached to each of lower and upper jaw members 63a and 63b and extend into camming grooves 93 for travel therein as a function of rotation of shaft 53 so that wheel 85 drives jaw assemblies 55 toward and away from each other in cyclic manner so as to slightly compress and slightly distend chamber walls 25 and 27 as previously described. Cam follower assemblies 95 and 97 are shown in FIG. 5 to be mounted to jaw assemblies 55 by machine screws extending from detents formed in jaw members 63a and 63b through apertures 101 formed therein.

As shown in FIG. 3, during the pumping action, upper and lower chamber walls 25 and 27 are moved to positions exterior or outward and interior or inward of the normal or "rest" configuration of chamber 9 as shown in FIG. 2. FIG. 3 shows in dotted lines, the movement both exterior and interior from the "rest" position. It is preferred that movement from this rest or neutral position be approximately 75% exterior or outwardly from the position and 25% interiorly or inward of the rest position. At no time do jaw assemblies 55 collapse walls 25 and 27 to totally shut off chamber 9. These parameters significantly reduce the stress normally generated at the round corners of the elastomeric tubes of the prior art. One of the unique aspects of this invention is that the movement as just described will reduce stress buildup and spalling of the walls as well as significantly increase the accuracy of the pump itself.

Valve means 103, operating as inlet and outlet valves, are shown in FIGS. 4, 5 and 8 to comprise a pair of C-shaped members 105, located outboard of handle means ends 21 and 23 and jaw assemblies 55 but interior of module ends 5, arranged to contact upper and lower module chamber walls 25 and 27. Members 105 are mounted in mutually aligned pairs, one above the other, and pivotally attached at their aft ends 107 to a pair of mounting pins 109, extending outward from chassis end walls 47. The fore ends 111 of members 105 are shown in FIGS. 4, 5 and 8 in mutual alignment, positioned above and below module 1 having pinch-off or chisel-shaped surfaces 113 formed thereon. A bias means 115 is provided for urging pinch-off surfaces 113 into mutual contact against module 1. As shown in FIG. 8, bias means 115 comprises a small coil spring 117 or other bias device attached between C-shaped members 105 at apertures 119 formed respectively in webbings 121 that are formed on the inside curvature of C-shaped members 105 and extending from fore ends 111 to aft ends 107.

Second cam and cam follower means 123 is provided for interconnection between shaft 53 and inlet and outlet valve means 103 for alternately causing pinch-off surfaces 113 to pinch off chamber walls 25 and 27 at locations laterally spaced apart from jaw assemblies 55 in controlled co-action with the rotation of shaft 53 to create an upstream location shown generally at 125 and a downstream location shown generally at 127 in module 1 to force fluid through lumen chamber 9 in controlled volumetric precision in the direction of the arrows shown in FIG. 4.

Means 123 is shown in part in FIG. 7c to comprise second camming groove 129 formed in second wheel face 91 for rotation about axis x—x as a function of powered shaft rotation. As shown in FIG. 6, a thin, elongated plate 131, preferably made of light metal such as aluminum, is arranged parallel to and adjacent second wheel face 91 in front of backing plate 45 and extends laterally between webbings 121 on C-shaped members 105. A short cam follower 133 is mounted on plate 131 and extends forward into second camming groove 129 for movement therein to drive plate 131 in a reciprocal pattern side-to-side between C-shaped members 105 as a function of rotation of shaft 53. A pair of spaced apart guide pins 135 protrude from chassis end walls 47 through slots 137 formed in plate 131 to guide the motion of plate 131 in a reciprocal path. Camming surfaces 139 are formed on opposite edges, preferably the top and bottom edges, of plate 131 and contact small cam follower wheels 141 mounted respectively in webbings 121. As motor 49 rotates shaft 53, second wheel face 91 and its respective camming groove 129 are set in motion.

Cam follower 133 is driven by camming groove 129 to cause plate 131 to oscillate from side to side between C-shaped members 105. Camming surfaces 139 are caused to press against cam follower wheels 141 by the action of bias means 115 bringing C-shaped members 105 into contact therewith. The narrowness of plate 131 at portions therealong allows coil springs 117 to bring pinch-off surfaces 113 into contact with pump module 1 and pinch down chamber 9. As slider cam plate 131 moves back and forth, camming surfaces 139 force cam follower wheels 141 and C-shaped members 105 apart thereby permitting re-establishment of the void in chamber 9 in pump module 1 so as to allow fluid to flow therethrough. Slider plate guide pins 135 retain slider cam plate 131 in its desired track. The overall effect is to coordinate the pinching off of chamber 9 by valve means 103 in coordination with the reciprocating movement of jaw assemblies 55 so as to provide pumping action in module 1.

Means 143 is provided for immediately unloading jaw assemblies 55, disconnecting jaw members 63a and 63b from module 1 and full opening inlet and outlet valve means 103 for changing pump module 1, the fluids, maintenance or emergency situations. Means 143 is shown in FIGS. 5 and 6 to comprise an elongated slider cam plate 145 having camming surfaces 147 formed on the top and bottom edges thereof, and arranged adjacent pump slider cam plate 131 and within the width of cam follower wheels 141. Elongated slider cam plate 145 is movable independent of pump slider cam plate 131 and further is arranged to reside in a "rest" position to one side of chassis 43 as shown in FIG. 5.

When it is desirable to replace module 1 or shut down the unit or otherwise, elongated slider cam plate 145 is manually moved from its rest position in the direction of the arrow, shown in FIG. 5, to force its cam surfaces 147 against cam follower wheels 141 to force open C-shaped members 105. In the embodiment shown in FIG. 4, a small angled detent 149 is formed in the four inside edges of C-shaped members 105 adjacent jaw assemblies 55. Small wheels 151 are pivotally mounted outside of jaw members 63a and 63b. Wheels 151 extend into detents 149 during normal operation of the pump and there is no contact between them. Upon shifting or movement of elongated slider cam plate 145 from its rest position, so as to force camming surfaces 147 against cam follower wheels 141 to open C-shaped members 105, the angled wall forming detent 149 contacts wheel 151 and forces the outer jaw members 63a from the inner jaw members 63b so as to overcome the pressure of bias means 115 and part groove portions 69 so as to release their grip on handle means 19 of module 1.

As shown in FIGS. 4 and 9, two separate pairs of C-shaped input occlusion sensor arms 153 are arranged, each pair in mutual-facing relationship, one pair upstream from pump module 1 outboard of valve means 103 and the other pair downstream outboard of downstream valve means 103. Sensor arms 153 are mounted at their aft ends 155 on mounting pins 109 and their fore ends 157 being arranged above and below module walls 25 and 27 respectively. Fore ends 157 are lightly spring-loaded through bias means 159 against top and bottom module walls 25 and 27. A magnet 161 is placed in one fore end 157 of each pair of sensors 153 and arranged adjacent one of module walls 25 or 27. An integrated circuit including a Hall-effect device 163 is placed in the other fore end 157 and arranged adjacent the other module wall 25 or 27. Due to the semi-flat shape of module chamber walls 25 and 27, internal pressures will expand the walls easily, and in turn spread the arms apart and change the distance between the magnet and the Hall-effect device giving a repeatable electrical output signal from IC 163 to the pump control electronics. Should the input become clogged or the tubing pinched, the semi-flat shape of walls 25 and 27 will change thereby bringing magnet 161 closer to or forcing it further away from the integrated circuit Hall-effect device 163 and providing an alerting change in the signal to the control electronics.

An air-in-line sensor 165 is located downstream from location 127, and comprises a similar pair of C-shaped output sensor arms 167 attached in mutual spaced-apart relation, one above the other, with their aft ends 169 pivotally mounted to pins 109 and held thereon with end caps 170. The fore ends 171 of arm 167 contain oval-shaped half grooves 173 that contact delivery line 175 extending downstream from pump module 1 and force the tubing into an oval shape, thereby putting the walls of the tubing in radial compression as shown in FIG. 10.

A piezoelectric transmitter 177 is located in one of fore ends 171 adjacent to walls of tubing 175 and a piezoelectric receiver 179 is mounted in the other fore end 171; both transmitter 177 and receiver 179 are positioned adjacent the walls of slightly flattened delivery line 175. When delivery line 175 is full of flowing fluid, an electrical signal is carried through the fluid and across the two oval-shaped wall segments into receiver 179. The slightest amount of air that passes between the receiver 179 and transmitter 177 disrupts the signal path thus giving an output signal change to the electronic controls so that an alarm may be sounded and the unit shut down to prevent ingestion of the air into the patient's body. Fore ends 171 are held together under pressure from bias means 181 that is shown in FIG. 10 to comprise a coil spring 183 fixed between apertures that are formed in webbings 185 formed on the inside of C-shaped arms 167. Cam follower wheels 187 mounted on webbings 185 are arranged for contact with camming surfaces 147 on elongated slider cam plate 145 to allow movement of the cam plate to cause opening of arms 167 to release the delivery lines from therebetween.

Another embodiment of the invention is shown in FIG. 5 and shows that jaw members 63a and 63b are mounted tightly together by screws 191 and bias means 73 such as coil spring 75 shown in FIG. 4 is eliminated. In this embodiment, detents 149 and small wheels 151 are also eliminated and the pump and pump module 1 is changed or removed from jaw assembly 55 by sliding it lengthwise along jaw assembly 55, in either direction i.e., either upstream or downstream, to slide handle means 19 from full groove 71 in jaw assemblies 55.

When inserts 29 are used in the ends of pump module 1, to provide the transition from the circular bore 39 to the interior configuration of lumen chamber 9, tab 41 may be added to end piece 31, as shown in FIG. 1b, to contact a small switch arm 193 that would be connected to the control circuitry. This would be used to provide for safety in preventing electric power to be transmitted to motor 49 as long as pump module 1 was not positioned correctly in jaw assembly 55. Upon insertion of module 1 along grooves 71, tab 41 would come into contact with switch arm 193 thereby arming the control circuitry so that the pump could thereafter function with pump module 1 fully seated in jaw assembly 55.

What is claimed is:

1. A volumetric fluid pump, comprising:
    (a) an infusion pump module comprising a length of resilient material having formed therein an elongated lumen chamber defined by broad, slightly rounded upper and lower chamber walls joined together along sharp side corners, said module having opposed, outwardly-facing top and bottom exterior graspable handle means extending along a portion thereof;
    (b) a chassis;
    (c) a shaft supported on said chassis for powered rotation about a fixed axis;

(d) a pair of elongated jaw assemblies pivotally attached to said chassis and arranged in spaced-apart, opposed juxtaposition, said assemblies configured to grasp said module handle means;

(e) first cam and cam follower means interconnected said shaft and said jaw assemblies for driving said assemblies as a function of powered shaft rotation in mutually opposed reciprocal motion to slightly distend and then slightly compress said pump module to produce a pumping motion;

(f) inlet and outlet valve means, spaced-apart from said jaw assemblies, and arranged for contact with said module spaced apart from said handle means; and, (g) second cam and cam follower means interconnected said shaft and said inlet and outlet valve means for driving said valve means to alternately pinch said module at spaced-apart locations in controlled coaction with said shaft to create an upstream and a downstream location on said module to force fluid there through in controlled volumetric precision.

2. The volumetric fluid pump of claim 1 further including means for determining the presence of occlusions in the fluid stream in said lumen chamber before that portion of the stream reaches a patient receiving the fluid to cause an abrupt shut-off of the pump and cessation of all fluid flow therein.

3. The volumetric fluid pump of claim 1 further including means for determining the presence of gas bubbles in the fluid stream in said lumen chamber after that portion of the stream exits said outlet valve to cause an abrupt shutoff of the pump and cessation of all fluid flow therein.

4. The volumetric fluid pump of claim 1 wherein said shaft is powered by an electric motor.

5. The volumetric fluid pump of claim 1 wherein said elongated jaw assemblies each comprise:
(a) a pair of jaw members each having part of a groove formed along one edge thereof;
(b) a hinge pin for pivotally mounting said members in side-by-side relationship to align said partial grooves into a full groove; and,
(c) bias means for urging said side-by-side pairs of jaw-members into close contact so that said partial grooves grasp said outwardly-facing handle means and retain them during operation of said pump.

6. The volumetric fluid pump of claim 5 wherein said graspable handle means includes an elongated first portion extending outward from said module separated therefrom by an elongated narrower second portion and where said partial groove, formed along said one edge of each said jaw member is of a shape conforming to the shape of said graspable handle means.

7. The volumetric fluid pump of claim 1 wherein said first cam and cam follower means includes:
(a) a wheel including first and second opposed wheel faces mounted normal to said shaft for rotation therewith;
(b) camming grooves formed in said first wheel face; and,
(c) first and second cam followers attached respectively to said jaw assemblies and extending into said grooves for travel therein to cause said assemblies to move toward and away from each other as a function of rotation of said shaft and said camming grooves.

8. The volumetric fluid pump of claim 1 wherein said inlet and outlet valve means includes:
(a) a pair of C-shaped members arranged in facing relationship with their respective ends in mutual alignment with one pair of said mutually aligned ends pivotally mounted to said chassis;
(b) pinch-off surfaces formed at the other ends of said mutually aligned C-shaped members arranged to receive said module therebetween spaced apart from said jaw assemblies; and,
(c) means for biasing said pinch-off surfaces into mutual contact.

9. The volumetric fluid pump of claim 8 wherein said second cam and cam follower means includes cam followers mounted on said C-shaped members for coaction with said second cam and cam follower means to cause said pairs of C-shaped members to pivot apart, against the pressure of said bias means and release the contact with said pinch-off surfaces from said module therebetween.

10. The volumetric fluid pump of claim 9 further including a planar member containing camming surfaces arranged for sliding engagement with said cam followers to produce movement of said inlet and outlet valve means.

11. The volumetric fluid pump of claim 10 wherein said planar member comprises a thin, elongated plate of terminal length defined by elongated spaced-apart edges, said edges having formed thereon camming surfaces for co-action with said cam followers on said C-shaped members to actuate the movement of said pinch-off surfaces.

12. The volumetric fluid pump of claim 11 wherein said camming surfaces are formed along said spaced-apart plate edges in a mirror-image pattern to cause equal movement of said C-shaped members and pinch-off surfaces against and away from said module therebetween.

13. The volumetric fluid pump of claim 9 wherein said cam followers are rollers mounted on said C-shaped members.

14. The volumetric fluid pump of claim 9 further including:
(a) camming grooves formed in said second wheel face; and,
(b) a cam follower attached to said cam member extending into said grooves for travel therein to drive said moveable cam member in reciprocal travel.

15. The volumetric fluid pump of claim 1 further including means for immediately unloading said jaw assemblies, disconnecting said assemblies from said module and opening said inlet and outlet valve means while said shaft is under powered rotation.

16. The volumetric fluid pump of claim 15 wherein said means for immediately unloading said jaw assemblies comprises an elongated member interconnected said inlet and outlet valve means and said second cam and cam follower means containing camming surfaces for co-action with said second cam and cam follower means upon sliding said elongated member from a passive position into an active position, to unload said valve means and cause widening and open said jaw assemblies to release said module.

17. The volumetric fluid pump of claim 1 wherein said elongated jaw assemblies each comprise:
(a) a pair of jaw members each having part of a groove formed along one edge thereof;

(b) a hinge pin for pivotally mounting said members in side-by-side relationship to align said partial grooves into a full groove; and, (c) attachment means for holding said side-by-side pairs of jaw-members into close contact so that said partial grooves grasp said outwardly-facing handle means and retain them during operation of said pump.

18. The volumetric fluid pump of claim 1 further including an insert, for placement in the distal ends of said infusion pump module, wherein said insert includes an end piece connected to a short insert segment, a circular bore is formed in said end piece for connection to a transfer line, and said bore passes through said short insert segment, flaring out as it passes there through to transition into the general size and shape of the internal chamber of said module.

19. The volumetric fluid pump of claim 1 further including an insert, for placement in the distal ends of said infusion pump module, wherein said insert includes an end piece connected to a short insert segment, a circular bore is formed in said end piece for connection to a transfer line, and said bore passes through said short insert segment for connection to the internal chamber of said module.

20. The volumetric fluid pump of claim 18 further including a tab extending from said end piece for contact with a switch to arm said motor when said insert and said module are fully inserted in said jaw assemblies.

21. The volumetric fluid pump of claim 19 further including a tab extending from said end piece for contact with a switch to arm said motor when said insert and said module are fully inserted in said jaw assemblies.

* * * * *